United States Patent [19]
Kwan

[11] Patent Number: 6,053,180
[45] Date of Patent: Apr. 25, 2000

[54] UV COMB

[75] Inventor: Koon-Chi Kwan, Kowloon, The Hong Kong Special Administrative Region of the People's Republic of China

[73] Assignee: China Pacific Trade Ltd., Tortola, Virgin Islands (Br.)

[21] Appl. No.: 09/310,154

[22] Filed: May 12, 1999

[51] Int. Cl.⁷ .............. A45D 7/02; A45D 24/10; A45D 1/04; A61N 21/00
[52] U.S. Cl. .......... 132/232; 132/212; 132/118; 132/229; 607/93; 607/94
[58] Field of Search .............. 132/232, 212, 132/219, 118, 227, 228, 229, 230, 233, 235, 148; 607/1, 88, 90, 94, 93; 604/20

[56] References Cited

U.S. PATENT DOCUMENTS

| | | | |
|---|---|---|---|
| 5,150,705 | 9/1992 | Stinson | 128/396 |
| 5,275,155 | 1/1994 | Changaris | 607/94 |
| 5,300,097 | 4/1994 | Lerner et al. | 607/93 |

*Primary Examiner*—John J. Wilson
*Assistant Examiner*—Robyn Kien Doan
*Attorney, Agent, or Firm*—Jacobson, Price, Holman & Stern, PLLC

[57] ABSTRACT

The present invention provides an UV light-emitting source in or adjacent to the styling portion of a hair and/or animal fur care or styling appliance.

The present invention incorporates an UV light emitting source into the hair styling appliance so that as the hair is being styled, the hair, the scalp as well as the appliance itself can be disinfected. Accordingly, while styling hair and/or fur, the present invention can facilitate the killing of microorganisms including spores, virus, fungus, bacteria and lice residing on hair and/or fur as well as on the appliance itself.

4 Claims, 18 Drawing Sheets

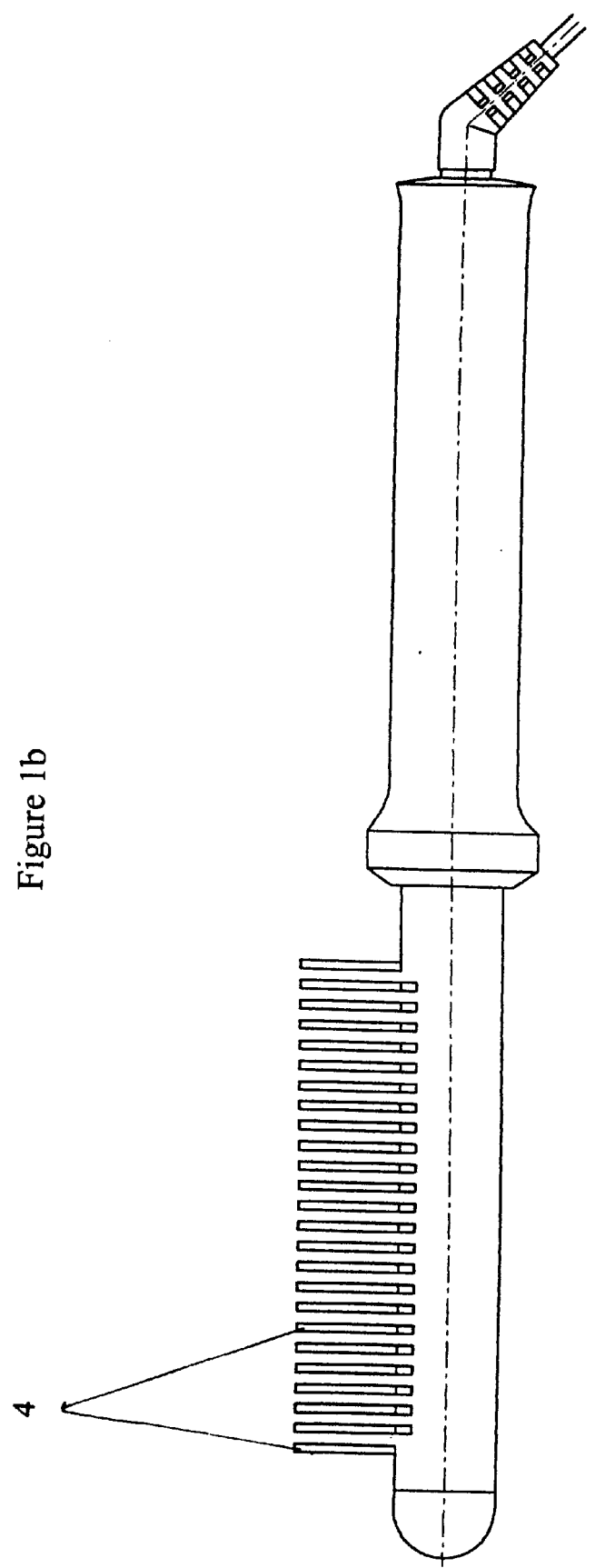

UV COMB

BACKGROUND OF INVENTION

1. Field of Invention

The present invention is related to improved appliances for hair and/or fur styling and caring.

2. Description of Prior Art

Appliances used for styling hair and fur are not new. These appliances include combs, curling irons and hairbrushes. There are a variety of these appliances. Some are modified so as to enhance the styling possibilities. For instance, some curling irons are equipped with a built in temperature control system so that the suitable temperature can be programmed according to different hair textures and the hairstyles desired.

Similarly, improvements can be introduced into the construction of comb so that while the hair is being styled, additional functions can also be achieved. For instance, some combs are designed in which the plurality of teeth members or projections have enlarged round endings so that as the hair is being styled, the scalp can be massaged at the same time.

Other variations of combs include introducing the plurality of combing teeth members or projections all around the spine of the comb. As a result, as the hair is being styled, the comb is rolled along the combing direction in order to achieve the desired hairstyle.

However, such conventional items may not address any problems associated with bacterial build-up in hair or animal fur, or on the appliance itself.

OBJECT OF THE INVENTION

It is the primary purpose of the present invention to provide a hair and/or fur care or styling appliance or which may provide some disinfection and sterilisation. In particular, it is the object of the present invention to provide easy to use hair care appliances in which styling and disinfecting can be performed at the same time or at least provide the public with a useful choice.

SUMMARY OF INVENTION

The present invention is, in general, concerned with improving the function of hair care or styling appliances, including but not limited to, combs, curling irons and hairbrushes.

Combs, curling irons and hairbrushes are used for styling hair. However, unless these hair styling appliances are cleaned frequently, dandruff, body oil and dirt tend to build up on the appliances over time. Bacteria and micro-organisms can take the opportunity to germinate on the appliances. These appliances can potentially become a breeding ground of these micro-organisms. Furthermore, bacteria and micro-organisms may reside in a person's hair or animal fur and may not be fully removed by washing.

Ultra violet is a type of electromagnetic wave having a wavelength of 180 to 400 mm. UV light is usually categorised into A wave, B wave, C wave and vacuum UV light. Ultra violet light (UV) is known to have a function to disinfect materials. UV light is widely used to disinfect materials especially in food processing and pharmaceutical production. The present invention incorporates an UV light emitting source into the hair styling appliance so that as the hair is being styled, the hair, the scalp as well as the appliance itself can be disinfected. UV light can kill micro-organisms including spores, virus, fungus, bacteria and lice.

Ultra violet is also known to produce ozone ($O_3$). Ozone is known to have a function of removing positive charged ions and have deodorising effects. Therefore, when a UV light hair appliance is being used, both the emitting UV light and the ozone produced by the UV light can disinfect and deodorise simultaneously while the hair is being styled and combed.

One advantage of the invention is that only one comb of each type is needed in a family as family members with less concerns that harmful bacteria will be transmitted among them. It is especially useful in hair saloons where hair styling appliances are shared by a number of hair stylists and used on many customers. As cleaning and disinfecting all appliances after being used by each customer each time is time consuming and cost-ineffective, the present invention may alleviate the problem by designing a series of hair styling appliances which can disinfect automatically when being used.

The present invention can also be applied on products used on domestic pets as well. It is generally agreed that taking care of the hygiene of pets and the need to frequently bath them can be troublesome. Additionally, dermatology problems are not unusual among pets. Some of these dermatology problems originated from bacterial infections. By using the present invention of an UV light emitting hairbrush, the skin of the pet can be disinfected as the fur is being combed.

The present invention has also a medical application as well. It is well known than UV light can alleviate rashes and acute infection. Therefore, the present invention provides a user friendly and cost-effective appliance to individuals having general chronic skin infection problems. Another characteristic of UV light is that skin will turn to tanner color when exposed to UV light. Therefore, the user of a UV light appliance can adjust the UV light source so that the desired skin color is resulted as the hair is styled.

Accordingly, the present invention is an appliance used for hair and/or fur care styling consists of a handle portion, a styling portion, an ultra violet light source, and a power supply assembly. The ultra violet light source is located in or adjacent to the styling portion of the said appliance.

BRIEF DESCRIPTION OF THE DRAWINGS

Preferred embodiments of the invention will now be described with reference to the following drawings in which:

FIG. 1b is a side view of FIG. 1a;

FIG. 1c is a cross sectional view of FIG. 1a;

FIG. 2b is a side view of the FIG. 2a;

FIG. 2c is a cross sectional view of FIG. 2a;

FIG. 3b is a side view of FIG. 3a;

FIG. 3c is a cross sectional view of FIG. 3a;

FIG. 4b is a side view of FIG. 4a;

FIG. 5b is a side view of the FIG. 5a;

FIG. 6b is a side view of FIG. 6a; and

FIG. 6c is a cross sectional view of FIG. 6a.

DETAILED DESCRIPTION OF THE PREFERRED EMBODIMENT

Figure 1A:
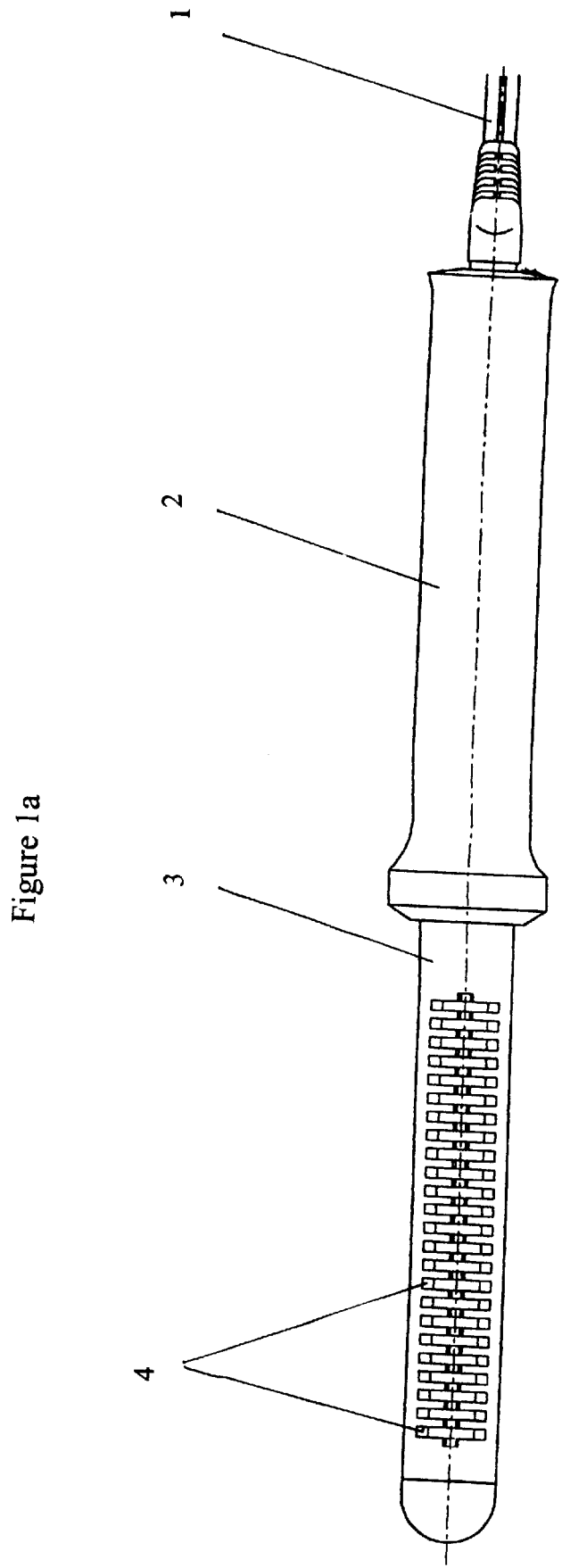
FIG. 1a is a top view of the UV light hair comb.

For purpose to promoting an understanding of the principles of the invention, reference will now be made to the embodiment illustrated in the drawings.

Figure 1C:
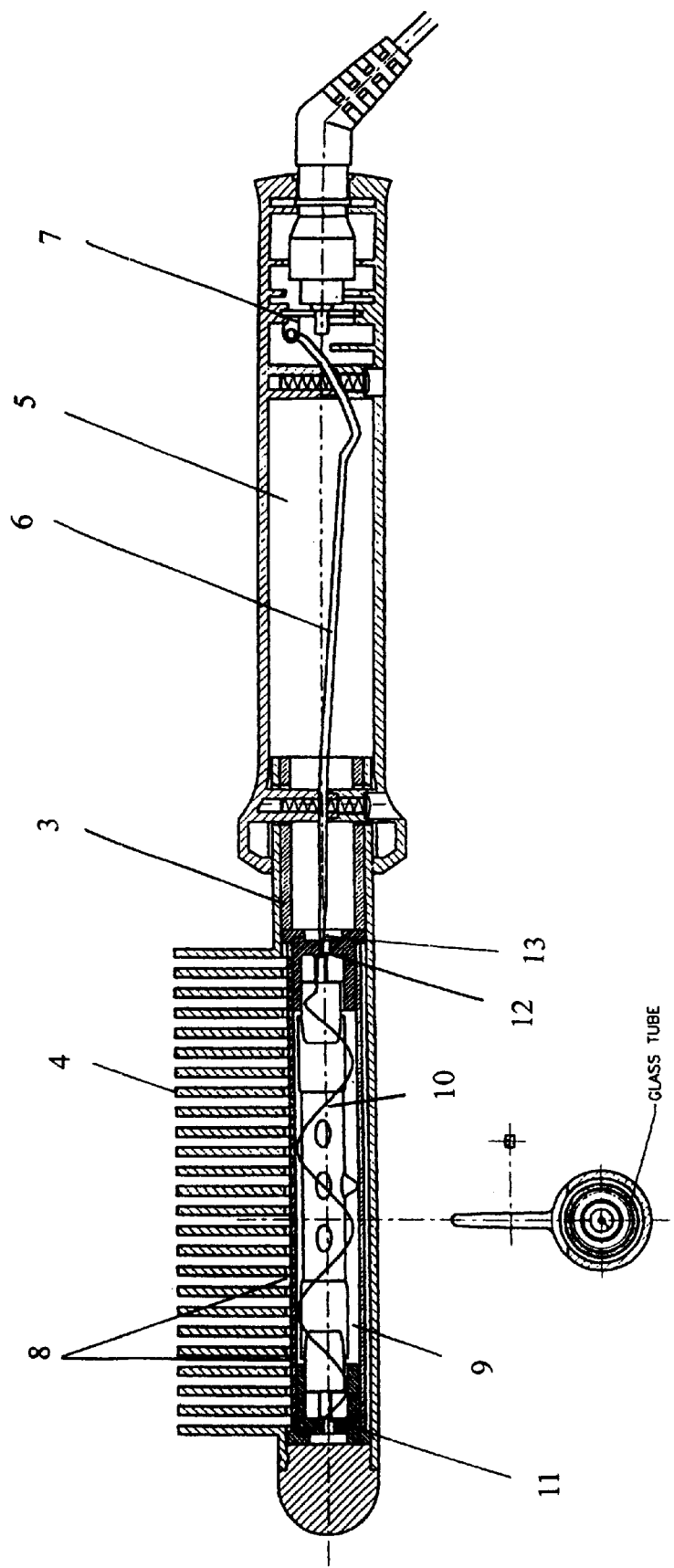

With reference to the drawings and in particular to FIGS. 1a, 1b and 1c thereof, the comb constructed according to the present invention mainly comprises a handle housing 2, an electrical cable 1, spine housing 3 and a plurality of teeth 4. The electrical cable 1 is connected to the power source when the preferred embodiment is being used. The handle housing 2 connects the electrical cable 1 and the spine housing 3.

The inside of the handle housing 2 comprises a hollow chamber 5, containing a power switching mechanism 7 and a conducting wire 6. The handle housing 2 is connected to the spine housing 3 on which a plurality of teeth 4 is provided.

The spine housing 3 has hollow chamber 9 where the UV light tube is located. The UV light glass tube 10 is installed and fixed between position 11 and 12 and is connected with a conducting wire 5 at location 13. Pluralities of openings 8 are located between the bases of the plurality of teeth 4 on the surface of the spine housing 3. Alternatively, openings or other means to allow emissions of the UV light could be provided in the teeth themselves.

When the power source of the preferred embodiment is switched on, electricity passing through the electrical cable 1 and conducting wire 6 will cause the UV light glass tube 10 to glow and emit UV light. As the hair is styled using the preferred embodiment, UV light is emitted through the plurality of openings 8 illuminating the combing surface. As hair or fur passes through the plurality of teeth 8, disinfection and sterilisation may occur. As UV light has a penetrating effect, the scalp will also be illuminated with the UV light so that the effect of disinfection can also be achieved on both the hair and scalp surface.

Figure 2A:
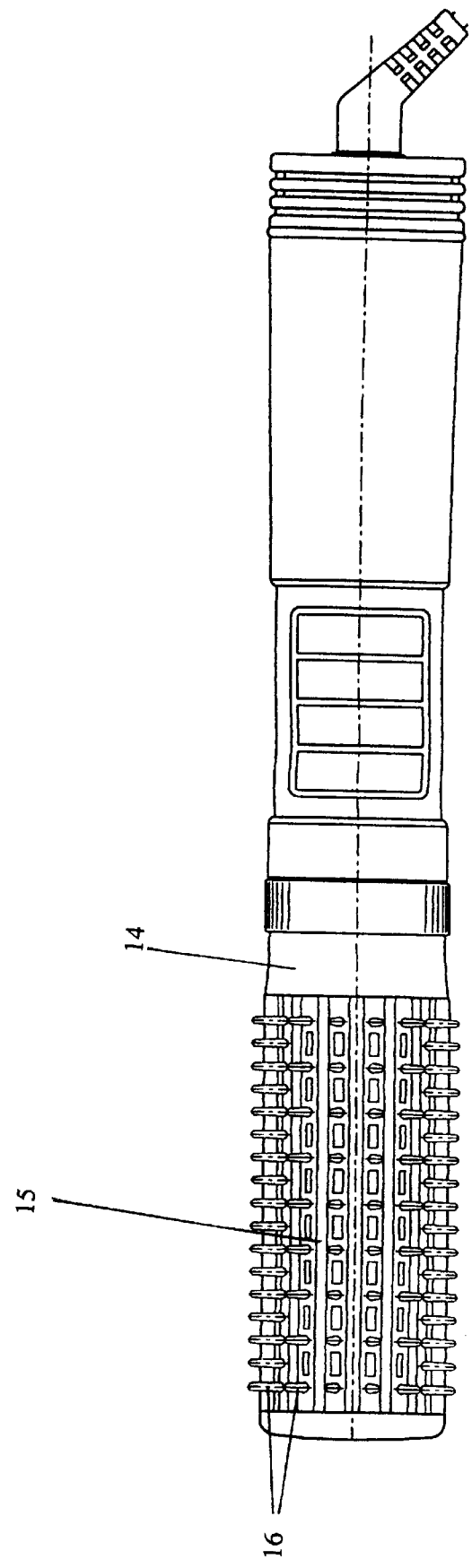
FIG. 2a is a top view of the second preferred embodiment of the UV light hair comb.
Figure 2B:
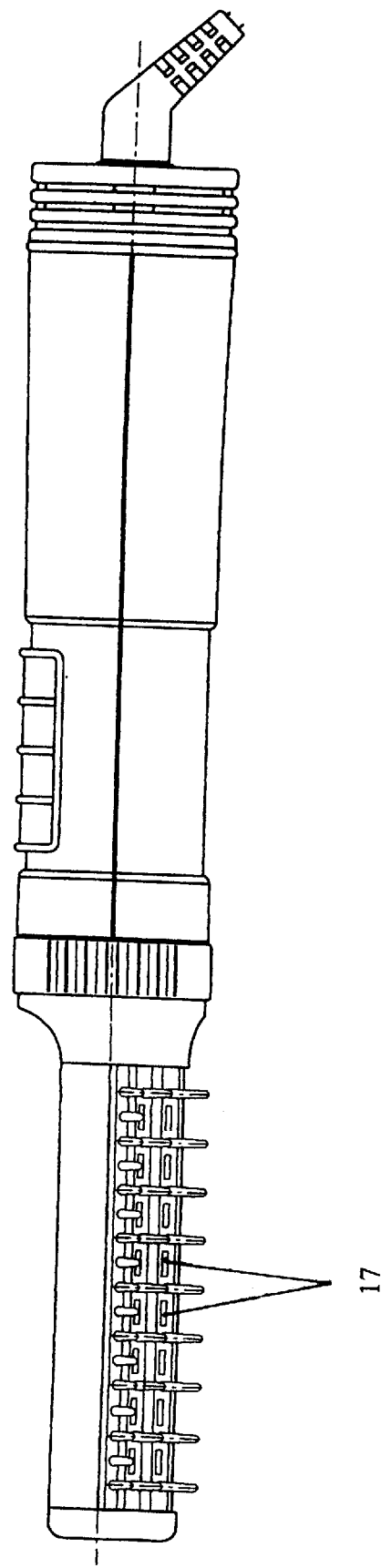
Figure 2C:
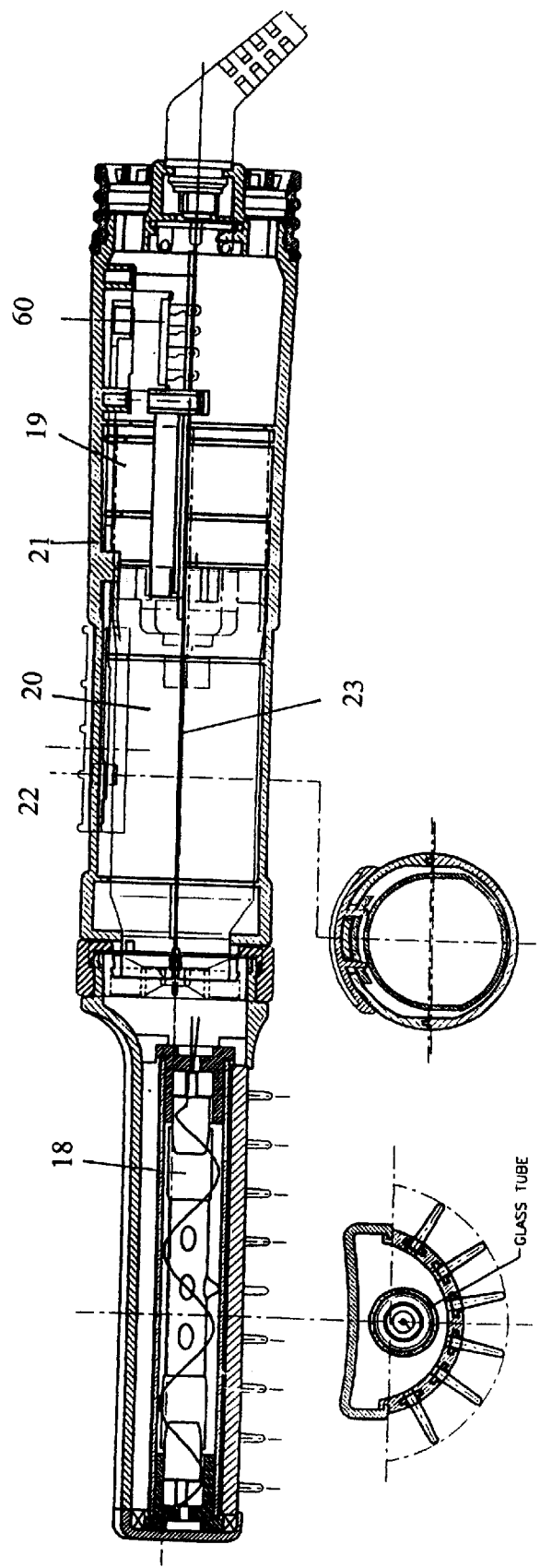

FIGS. 2a, 2b and 2c show another preferred embodiment of the present invention. In this embodiment, the spine housing 14 has a modification of which a larger two-dimensional surface 15 where a plurality of rows of teeth members 16 are located. This preferred embodiment also has a built in heating source 20, a motor 19 and a fan 18 located inside the handle housing 21. When the trigger 22 is switched on, electricity passes through the electrical cable 23, to the motor 19 which rotates the fan 60, and the UV light glass tube 18. As a result, warm air is blown through the openings 17. UV light emitting from the UV light tube 16 will also emit through the 20 openings 17. As a result, the hair being styled with the teeth members 16 and the hot air generated by the heating assembly 20 may also be disinfected by the UV light emitted from the UV light tube 18.

Figure 3A:
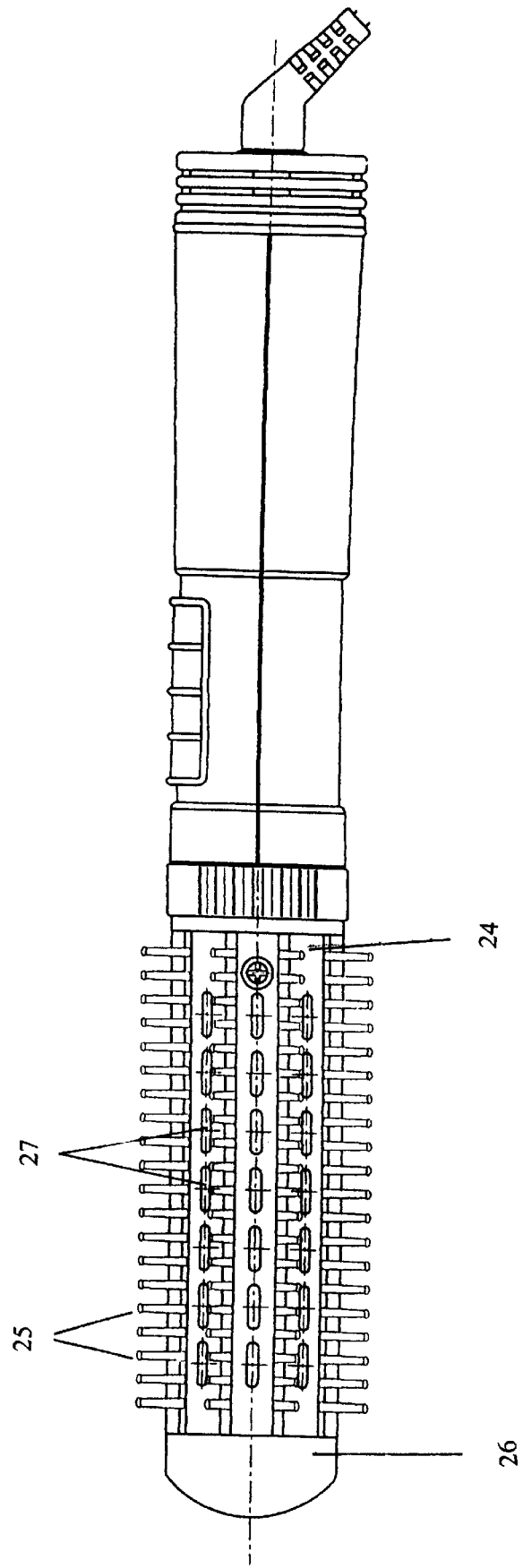
FIG. 3a is a top view of the third embodiment of an UV light hairbrush.
Figure 3B:
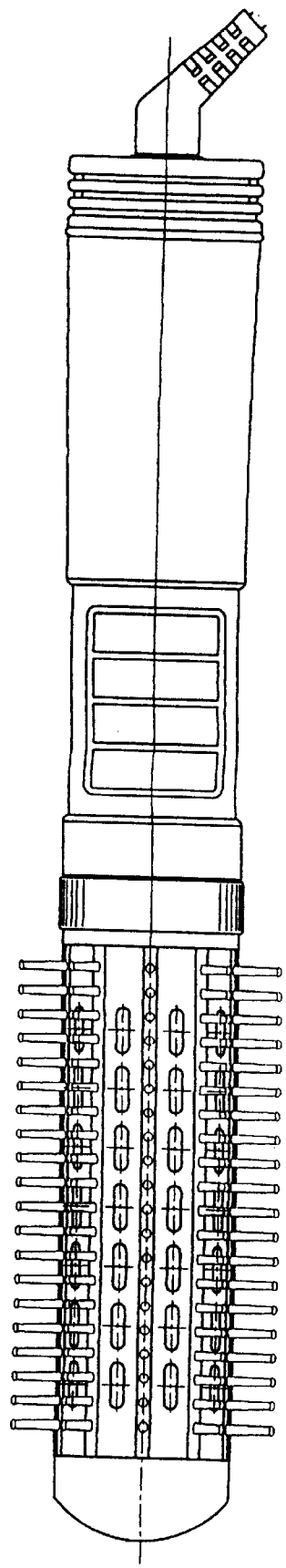
Figure 3C:
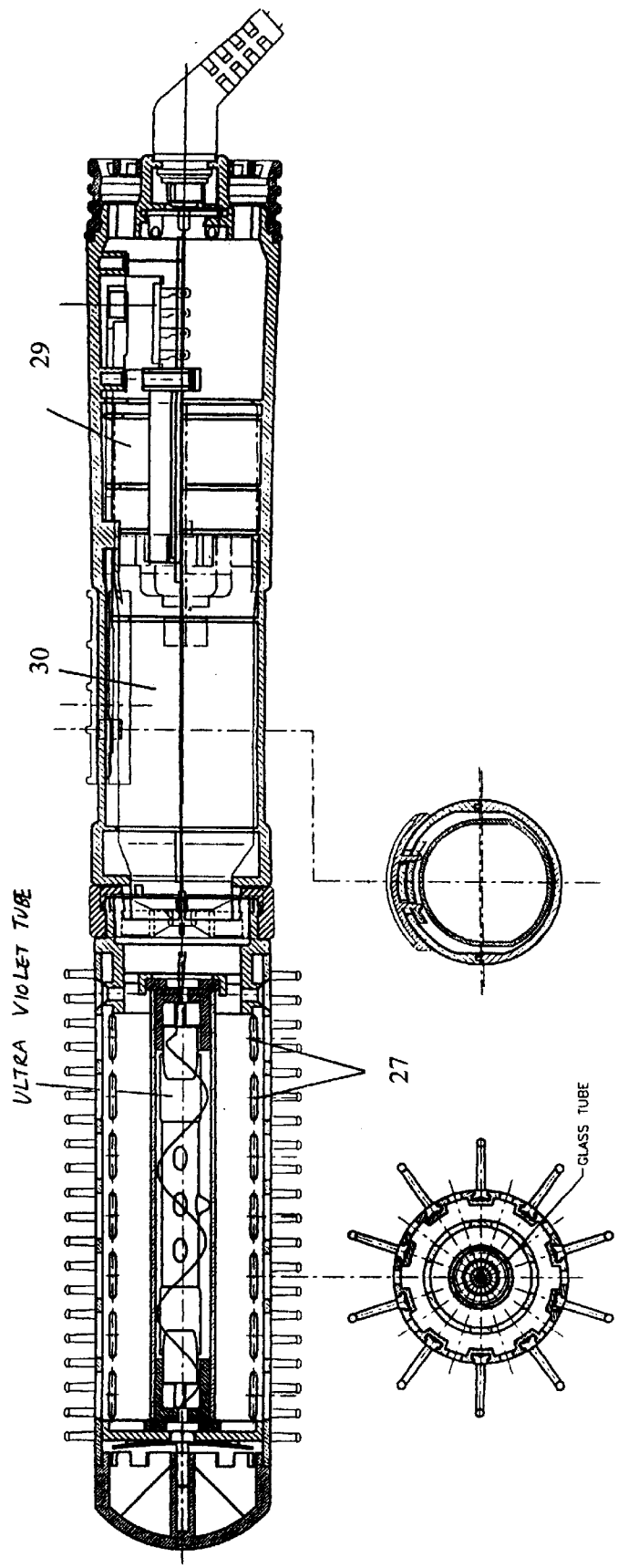

FIGS. 3a, 3b and 3c show another preferred embodiment of the present invention, wherein the entire outer surface 24 of the spine housing 26 has a plurality of rows of teeth members 25 and openings 27. Hot air generated by the fan assembly 29 and heater assembly 30 is blown through the openings 27. UV light generated by UV light tube is also emitted through the openings of 27.

Figure 4A:
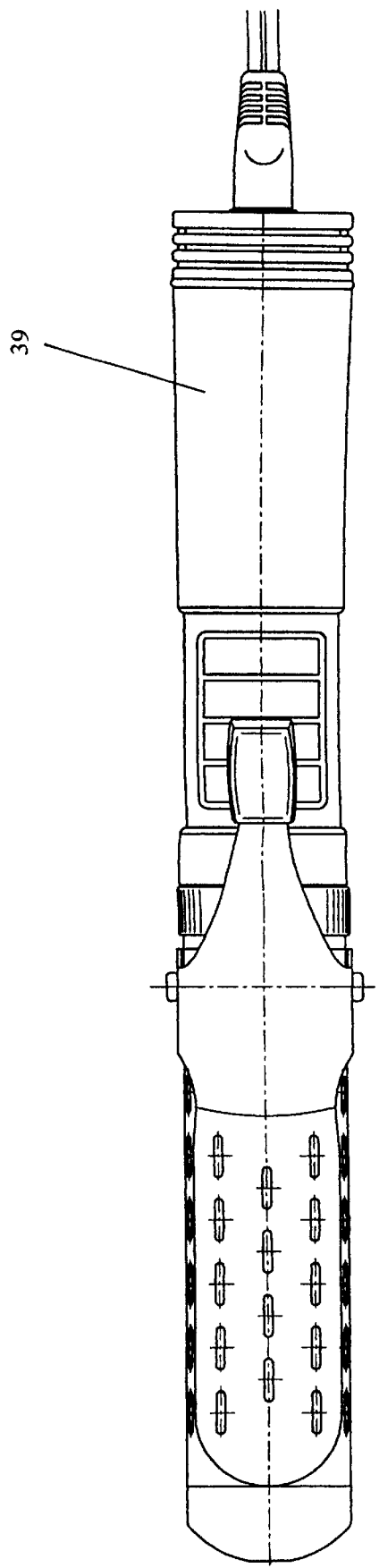
FIG. 4a is a top view of the fourth preferred embodiment of the UV light hair curling iron.
Figure 4B:
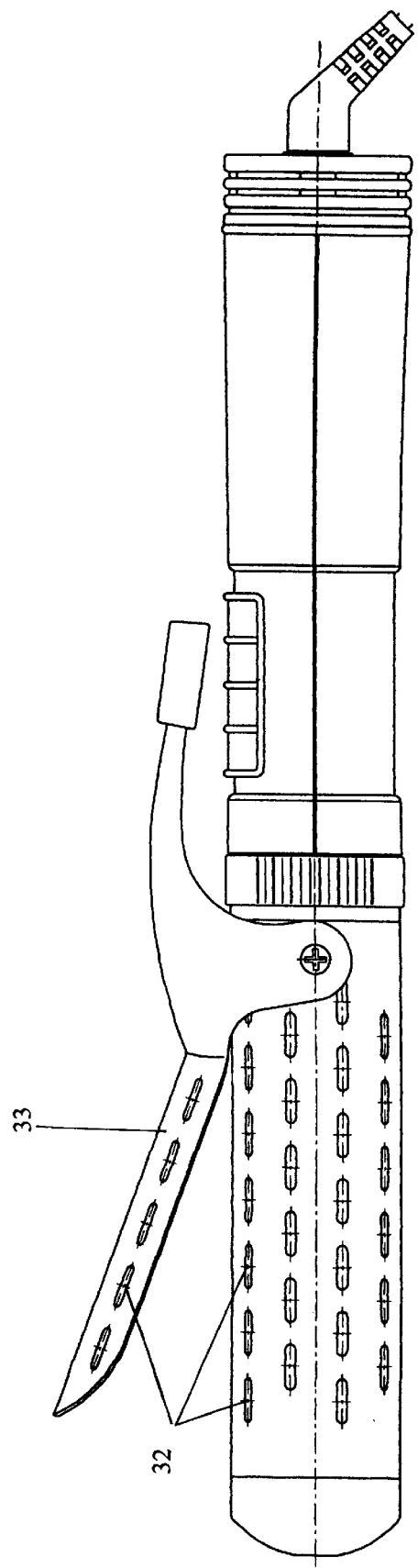
Figure 4C:
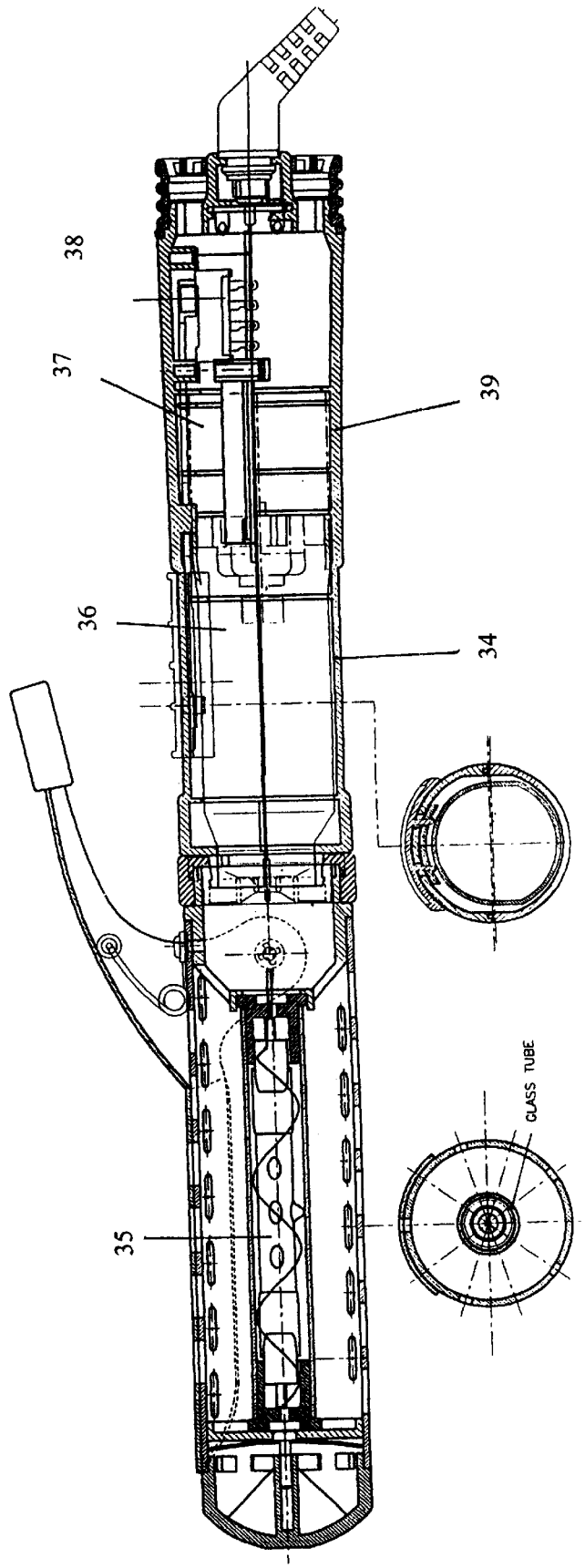
FIG. 4c is a cross sectional view of FIG. 4c.

With reference to the drawings of FIGS. 4a, 4b and 4c, this preferred embodiment is a hair appliance which is a hair curling iron according to the present invention. This preferred embodiment comprises a handle housing 39, wherein a heater assembly 36, a motor 37 and a fan assembly 38 are contained inside the handle housing 39. The heating housing 34 is connected adjacent to the handle housing 39. The ironing lever 33 is attached the heating housing 35. There is a plurality of openings 32 located on the surface of the entire heating housing 34. The UV light tube 35 is located inside the heating housing. As the trigger 40 is switched on, warm air flowing through the openings 32 can curl the hair between the lever 33 and the exterior of heating housing 34. At the same time, UV light emitting through openings 35 may disinfect the hair and the scalp underneath.

Figure 5A:
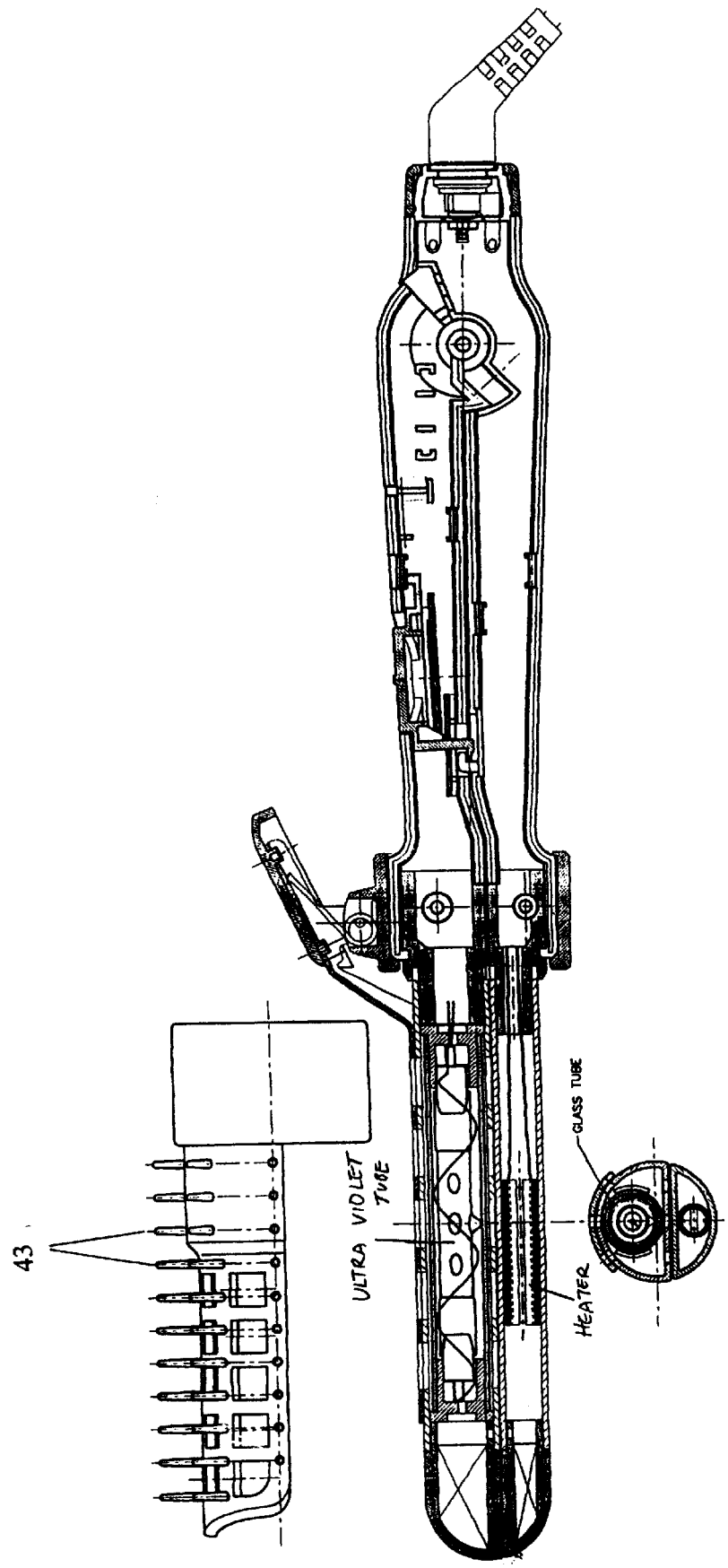
FIG. 5a is a top view of the fifth preferred embodiment of the hair curling iron.
Figure 5B:
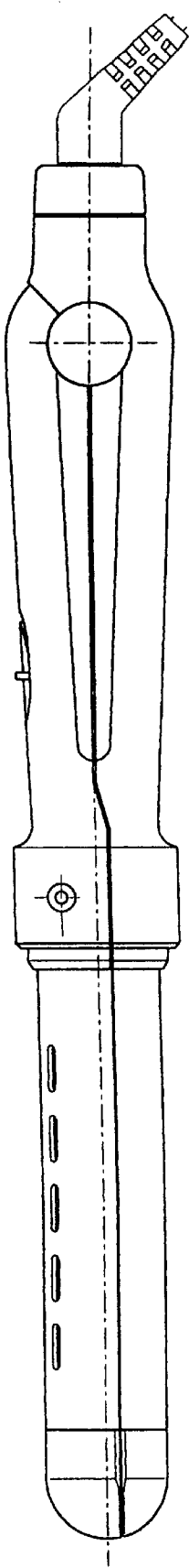
Figure 5C:
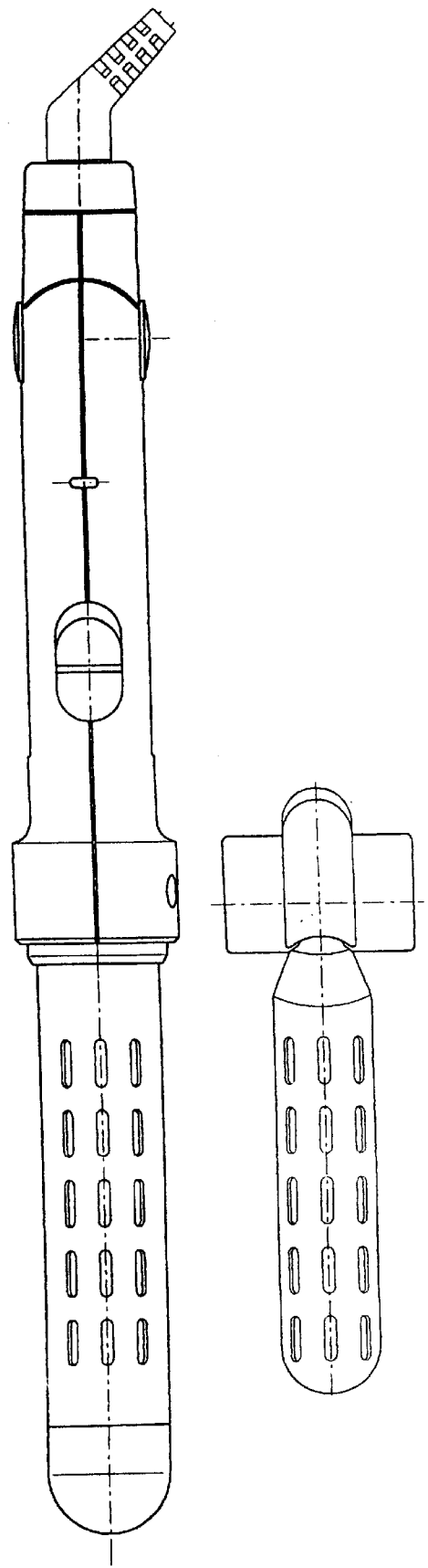
FIG. 5c is a cross sectional view of FIG. 5c.

FIG. 5a illustrates another embodiment similar to that in FIG. 4a. This preferred embodiment has additional combing teeth members 43. The additional feature allows this embodiment to carry out the functions of curling, disinfecting and combing simultaneously.

Figure 6A:
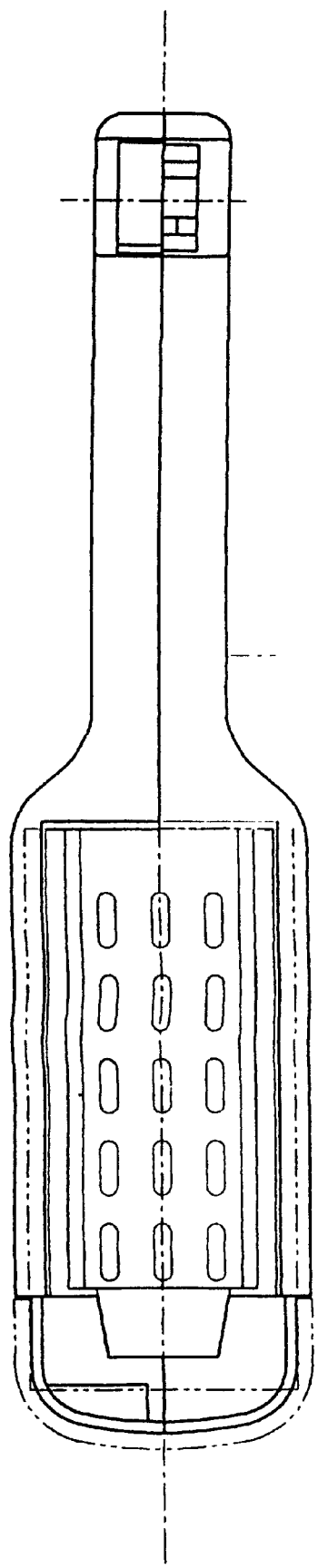
FIG. 6a is a top view of the sixth preferred embodiment of the hair curling iron.
Figure 6B:
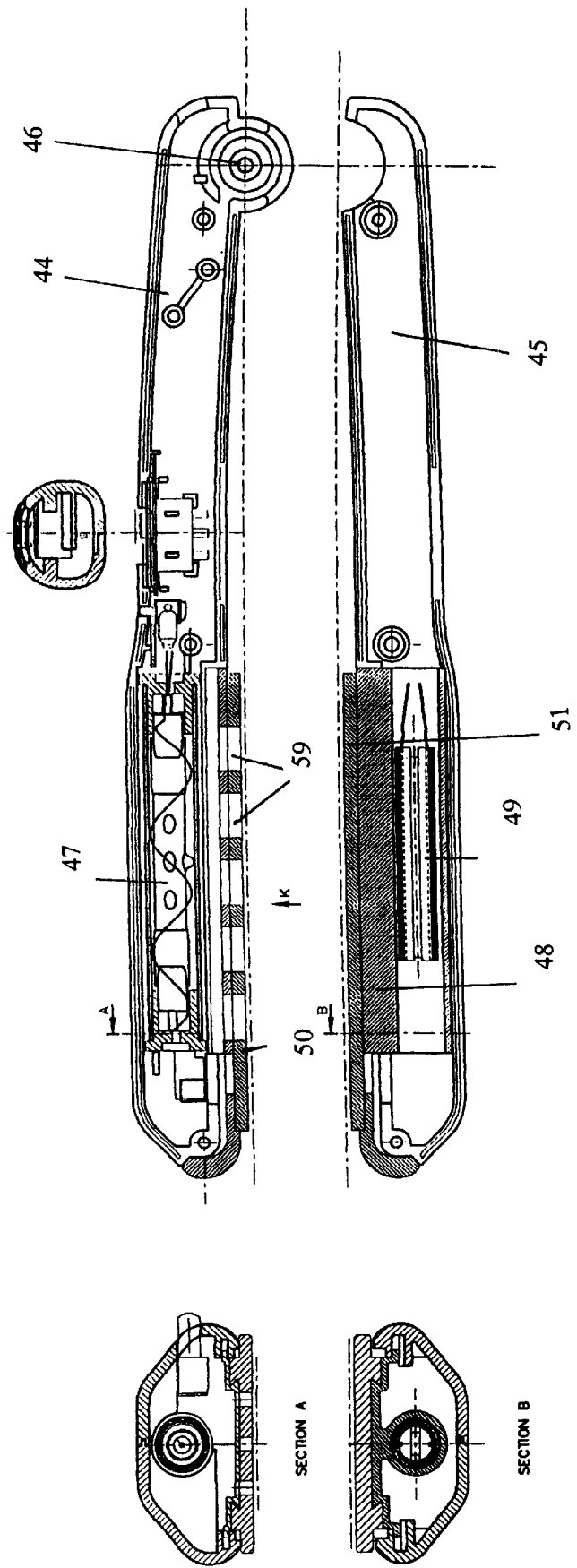
Figure 6C:
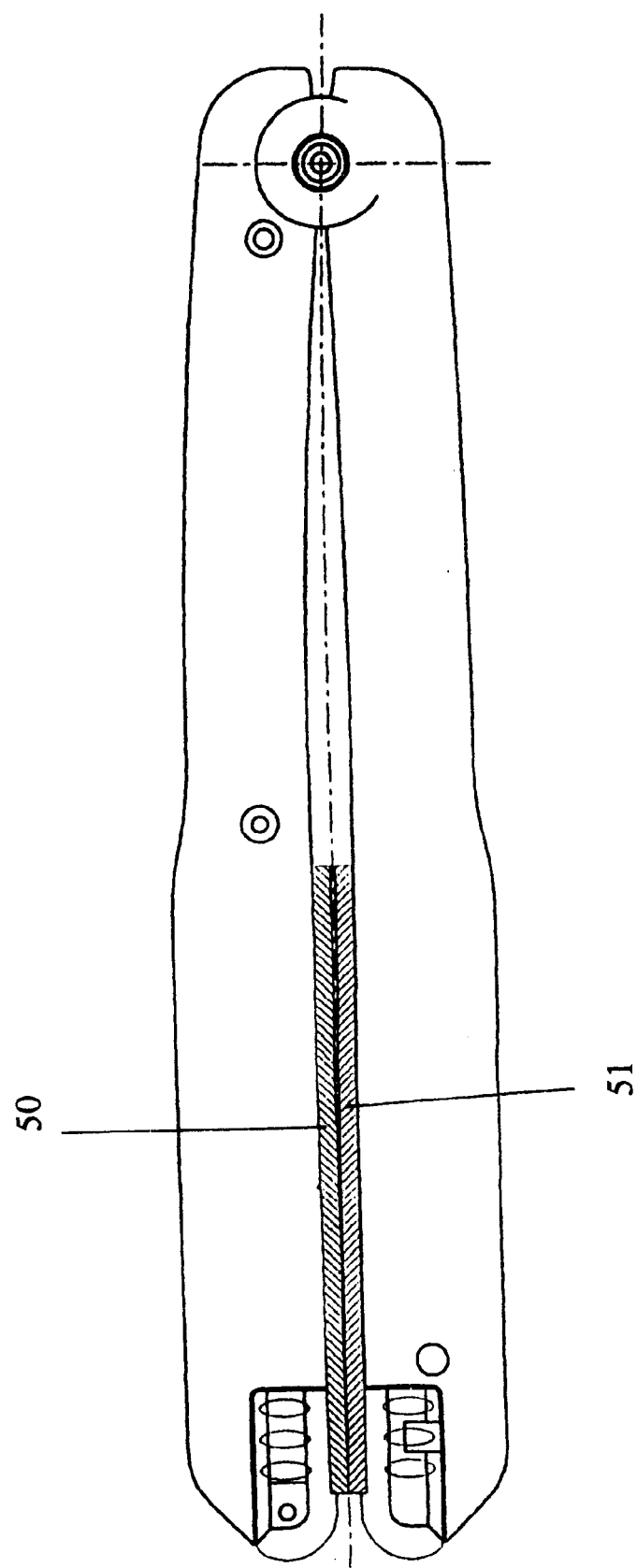

FIGS. 6a, 6b and 6c show a sixth preferred embodiment according to the present invention. This embodiment includes of two housing members 44 (the upper housing member) and 45 (the lower housing member). The upper housing member 44 and lower housing member 45 are joined by a hinge 46. The upper housing member 44 contains an UV light tube 47 and a plurality of openings 59 are located on the emitting surface 50 of the upper housing member 44. The lower housing member 45 consists of a heating assembly 49, a heat conducting plate 48 and an ironing surface 51.

When the power source is switched on, the UV light tube will glow emitting UV light through the openings 46 and the heat generated from the heating assembly 49 is conducted along conducting plate 58 heating up ironing surface 51. Hair located between ironing surface 51 and emitting surface 50 is styled by the heat source and disinfected by the UV light.

In general, the embodiments described have provided the UV light in conjunction with the hair care appliance such that the hair is treated during the styling operation. Although the embodiments disclosed have provided the UV light within the styling portion of the apparatus, other arrangements are possible to provide the UV light emitting device adjacent the styling portion such that the light may be emitted over the styling portion but not from within the styling portion as disclosed in these embodiments. For example, a conventional styling portion may be utilized with an UV light adjacent and directed on to the styling portion connected to either the styling or handle portions of the device.

These preferred embodiments include the UV light within the styling portion to emit from the styling portion. In the case of styling portions with teeth such as for a comb or other radially extending styling portions, the UV light may be emitted between or from the teeth.

In general, an UV light source is provided in the form of a tube, which already has a glass, or similar outer surface through which the UV light may emit. With the UV light source provided in such a manner, it may be sufficient to provide apertures suitably spaced along the styling portion through which the UV light may pass. Alternatively, panels of these styling portion could be provided with a specific material to allow the passage of UV light. In a yet further possibility, the entire styling portion could be made from a material which allows the passage of at least some UV light.

Alternatively, a focusing lens can be placed adjacent to the UV light source so that the intensity of the UV can be adjusted according to the user's requirements. For instance, if a high intensity of UV light is desired, the focusing assembly can be adjusted accordingly to achieve the desired UV intensity.

With regard to control means for the apparatus, it is generally intended for these preferred embodiments that the UV light is emitting while the styling apparatus is in operation. As such, power may be provided to the UV light tube as soon as the apparatus is switched on for such other operations it may perform such as acting as a curling iron. In such a manner, there is no need for separate control for the UV light tube from the main control for the curling apparatus itself. Nevertheless, it is envisaged that other embodiments could employ a separate control for the UV light. This may allow independent operation of the UV light.

Although generally intended for emission of the UV light while the hair is being styled, if only disinfection between users of the apparatus is required, the UV light tube may be operated only when the apparatus is not in actual use. For example, in the case of an apparatus being used by a hair saloon or similar, it may be desirable for the apparatus to emit the UV light for a self-cleaning operation between users if it is not desired during the styling operation itself.

Generally such apparatus may be provided with some independent control for the UV light so that it may at least be switched off during the styling process if it is intended for use in hair saloons or similar. In such circumstances, there may be UV-sensitive customers that may not wish the light to be emitted during the styling operation.

The power source for the UV light can be any suitable power source which, in the case of styling apparatus which utilized a power source for other functions, may utilize that power source for the UV light emission as well. Alternatively, an independent power supply could be provided to the UV light.

In general, the materials for construction of such apparatus will be those suitable materials for hair care or styling apparatus. Generally, such apparatus are provided with outer surfaces made from plastic or similar materials. If the UV light is provided in the form of its own tube, it is merely necessary to provide apertures in the plastic material to allow emission of the UV light. Alternatively, panels of material capable of allowing passage of UV light could be incorporated.

Thus it can be seen that the present invention provides a variety of appliances which may be used for the care or styling of hair or animal fur. The embodiments all include an UV light source to emit light onto the hair or fur during the styling operation.

Specific language is used above to describe the preferred embodiments. Nevertheless, no limitation of the scope of the invention is thereby intended, such alternations and such further applications of the principles of the invention as illustrated herein being contemplated as would normally occur to one skilled in the art to which the invention relates.

The invention as described is deemed to incorporate equivalents to the integers recited where such equivalents would be apparent to those skilled in the art. The description is provided by way of example only.

I claim:

1. A hair or fur styling appliance comprising:

a handle portion;

a styling portion;

an ultra violet light source; and wherein the said ultra violet light source is located in the styling portion of said appliance and said ultra violet light source emits through at least one UV light transmittable portion in a housing of said styling portion; and wherein said UV light transmittable portion comprises a plurality of apertures in said housing of said styling portion.

2. A hair or fur styling appliance as claimed in claim 1 wherein said ultra violet light source is provided within said styling portion.

3. A hair or fur styling appliance as claimed in claim 1 wherein said handle portion is connected to said styling portion adjacent an end of said styling portion.

4. A hair or fur styling appliance as claimed in claim 1 wherein said ultra violet light source is operable under the control of control means to emit ultra violet light during use of said styling portion to treat hair or fur, scalp or skin and the styling portion itself throughout the styling operation.

* * * * *